United States Patent
Humphrey (10) Patent No.: US 8,945,234 B2
(45) Date of Patent: Feb. 3, 2015

(54) PROSTHESIS HAVING A METAPHYSEAL ELEMENT

(71) Applicant: Optimus Orthopedic Designs LLC, Eagle, ID (US)

(72) Inventor: C. Scott Humphrey, Eagle, ID (US)

(73) Assignee: Optimus Orthopedic Designs LLC, Eagle, ID (US)

( * ) Notice: Subject to any disclaimer, the term of this patent is extended or adjusted under 35 U.S.C. 154(b) by 71 days.

(21) Appl. No.: 13/869,893

(22) Filed: Apr. 24, 2013

(65) Prior Publication Data
US 2013/0289738 A1    Oct. 31, 2013

Related U.S. Application Data

(60) Provisional application No. 61/638,817, filed on Apr. 26, 2012.

(51) Int. Cl.
*A61F 2/30* (2006.01)
*A61F 2/40* (2006.01)
(Continued)

(52) U.S. Cl.
CPC ............... *A61F 2/30* (2013.01); *A61F 2/4059* (2013.01); *A61F 2/30744* (2013.01); *A61B 17/1684* (2013.01); *A61B 17/842* (2013.01); *A61F 2002/2835* (2013.01); *A61F 2002/30153* (2013.01); *A61F 2002/30176* (2013.01); *A61F 2002/30322* (2013.01); *A61F 2002/30405* (2013.01); *A61F 2002/30561* (2013.01); *A61F 2002/30777* (2013.01); *A61F 2002/3093* (2013.01); *A61F 2002/30932* (2013.01);
(Continued)

(58) Field of Classification Search
USPC .......... 623/18.11, 19.11–19.14, 22.11, 22.15, 623/22.4, 23.15, 23.18, 23.19, 23.2, 623/23.23–23.26, 23.28, 23.33, 23.35, 623/23.44
See application file for complete search history.

(56) References Cited

U.S. PATENT DOCUMENTS 4,978,357 A * 12/1990 Goymann et al. ........... 623/22.4
6,165,224 A * 12/2000 Tornier ...................... 623/23.21
(Continued)

OTHER PUBLICATIONS

International Searching Authority, International Search Report and Written Opinion of the International Searching Authority, Jul. 18, 2013, 12 pages, Application No. PCT/US2013/038180, International Search Authority, U.S. Receiving Office.
(Continued)

*Primary Examiner* — Marcia Watkins
(74) *Attorney, Agent, or Firm* — Holland Law Office P.L.L.C.

(57) ABSTRACT

The present invention is directed to a prosthesis for an arthroplasty in a long bone and a methods for achieving a press fit of the metaphyseal element of the prosthesis into a metaphysis of the long bone and the extraction of the prosthesis when indicated. The prosthesis includes a metaphyseal element attached at a proximal end of a stem, the metaphyseal element of the prosthesis is configured to optimize placement of bone marrow about, and in some embodiments, within the metaphyseal element to achieve a press-fit in the metaphysis of the long bone. The prosthesis also includes one or more apertures formed in the joint base member of the prosthesis. Preferably each slot includes a frangible wall which is readily penetrated to accommodate passage of an osteotome of other tool to break the metaphyseal element free from bony in-growth that occurs against the metaphyseal element.

10 Claims, 7 Drawing Sheets

(51) Int. Cl.
 *A61F 2/32* (2006.01)
 *A61B 17/16* (2006.01)
 *A61B 17/84* (2006.01)
 *A61F 2/28* (2006.01)
 *A61F 2/46* (2006.01)

(52) U.S. Cl.
 CPC . *A61F2002/4022* (2013.01); *A61F 2002/4062* (2013.01); *A61F 2002/4066* (2013.01); *A61F 2002/4619* (2013.01)
 USPC .................. 623/23.42; 623/22.42; 623/22.43; 623/19.14; 623/23.43

(56) References Cited

U.S. PATENT DOCUMENTS

| | | | |
|---|---|---|---|
| 6,171,341 | B1 | 1/2001 | Boileau et al. |
| 6,334,874 | B1 | 1/2002 | Tornier et al. |
| 6,406,496 | B1 | 6/2002 | Ruter |
| 6,899,736 | B1 | 5/2005 | Rauscher et al. |
| 7,186,269 | B2 | 3/2007 | Cyprien et al. |
| 7,531,003 | B2 | 5/2009 | Reindel |
| 7,556,652 | B2 | 7/2009 | Angibaud et al. |
| 8,187,336 | B2 | 5/2012 | Jamali |
| 2007/0118230 | A1 | 5/2007 | Callaway |
| 2011/0218638 | A1* | 9/2011 | Termanini .................. 623/22.15 |
| 2012/0041564 | A1 | 2/2012 | Landon |
| 2012/0101583 | A1 | 4/2012 | Lascar et al. |

OTHER PUBLICATIONS

Boorman, M.D., Richard S., "A conservative Broaching and Impaction Grafting Technique for Humeral Component Placement and Fixation in Shoulder Arthroplasty: The Procrustean Method", Techniques in Shoulder & Elbow Surgery, 2001, vol. 2(3), pp. 166-175.

* cited by examiner

PROSTHESIS HAVING A METAPHYSEAL ELEMENT

RELATED APPLICATION

This application claims the benefit of the filing date of U.S. Provisional Patent Application No. 61/638,817 filed Apr. 26, 2012 entitled Prosthesis Having a Metaphyseal Portion and a Method for Achieving a Press-Fit of the Metaphyseal Portion.

BACKGROUND OF THE INVENTION

1. Field of the Invention

The present invention relates to arthroplasty and devices and methods for joint replacement and more specifically to a metaphyseal element of a prosthesis and methods of installing and removing such a prosthesis.

2. Background

The use of implantable hip and shoulder prosthesis systems is well known in the prior art. A widely used configuration of such prosthetic devices includes a stem intended for insertion into the prepared end of long bone to which the device is to be fit for joint reconstruction. A head including cooperative joint element is fixed or fixable to the stem. Depending on the particulars of any given design for such a prosthesis, there may be a distinguishable metaphyseal element of the prosthesis that provides a transition between the stem and the head.

Fixation of the stem of the prosthesis within the intramedullary bone has been, as seen in the prior art, achieved press-fitting the stem into the intramedullary bone or in the alternative by cementing the stem of the prosthesis upon insertion into the shaft of the bone. According to the prior art, the stem of a press-fit prosthesis typically has a textured or roughened surface or surface coating. Such a prosthesis achieves initial bony fixation from the hoop stresses and friction associated with the interference fit that occurs as the device is forcibly inserted into the bone. Over time the bone remodels, leading to a change in the mode of fixation. The hoop stresses and interference fit diminish as the bone remodels with time, and eventually the primary mode of fixation becomes fusion between the roughened prosthetic surface and the native bone. The robust bone-to-prosthesis fusion that occurs along the length of roughened or coated stem makes the prosthesis difficult to remove without destroying the bone. Additionally, while this technique may provide good fixation for a period of time, the strong fixation that occurs from bony fusion to the distal aspect of such a prosthesis will later cause stress shielding of the proximal bone, eventually leading to a proximal osteolysis that leaves the bone/stem fit predisposed to loosening and the bone predisposed to fracture over time. Similarly, in an arthroplasty where cement has been used to secure the stem of the prosthesis in the shaft of the bone, fixation of the stem to the bone by cementing can be to such an extent that bone is destroyed while freeing the stem for removal. Removal of a humeral prosthesis in the reverse shoulder arthroplasty setting is made even more difficult because the proximal shell of the humeral prosthesis physically limits the surgeon's ability to apply surgical instruments such as an osteotome to free the prosthesis from the bone in the metaphyseal and diaphyseal regions.

Therefore one object of the present invention is to provide a prosthesis for a joint replacement specifically adapted to achieve secure fixation of the prosthesis to the bone by promoting osseous integration in the metaphysis, while eliminating settling, loosening or rotation of the device with respect to the bone. Another object of the present invention is to provide a press-fit shoulder prosthesis optimized for a bone grafting technique. Because bony in-growth occurs ideally in the metaphysis, another object of the present invention is to provide a shoulder prosthesis including a metaphyseal element adapted to promote osseous integration in the metaphyseal region. Another object of the present invention is to provide a press-fit shoulder prosthesis optimized for a bone grafting technique that is also optimized to increase the surface area in the metaphyseal portion of the prosthesis where bony ingrowth/ongrowth may occur, to promote bony ingrowth against and about the metaphyseal region of a shoulder prosthesis. Another object of the present invention is to provide a press-fit shoulder prosthesis that is optimized for ease of removal with minimal trauma to the bone.

Another object of the present invention is to provide a press-fit shoulder prosthesis that reduces inventory costs insofar as the press-fit shoulder prosthesis may be configured so as to be employed for multiple and various indications including as a primary press-fit prosthetic device, a cemented prosthetic device, or a fracture stem/prosthetic device.

SUMMARY OF THE INVENTION

These and other objects may be met by the present invention which is directed to a prosthesis for a joint replacement that includes a metaphyseal element adapted for optimal osseous integration and methods for achieving a press-fit of the metaphyseal element of the prosthesis within the cavernous metaphyseal region of the bone to eliminate settling, loosening or rotation of the device with respect to the bone and for extracting the prosthesis.

In a preferred embodiment, the prosthesis includes a stem adapted for fitting into the shaft of a bone to which the device is to be fit for joint reconstruction. A metaphyseal element is attached at a proximal end of the stem and a joint element is attached at a proximal end of the metaphyseal element. The joint element includes an articulation surface configured as a ball, a socket or a cup.

The metaphyseal element of the prosthesis provides a transition between the stem and the head. In the preferred embodiment, the metaphyseal element includes two or more wall segments that are fixed to the stem and extend proximally from the stem. A joint base member is attached at a proximal end of the metaphyseal element and a joint articulation member is then attached to the joint base member. The wall segments include a substantially flat outer surface that is coated or textured to promote bony in-growth against the surface of the wall segment. A slot is formed in the joint base member above each of the substantially flat outer surfaces of the wall segments, the slot extending through the base member of the joint element. In the event that removal of the prosthesis is indicated following installation and bony in-growth against the outer surfaces of the metaphyseal element, a tool such as an osteotome may be inserted through each of the slots and worked down along the flat face of each of the wall segments to free the prosthesis. In this respect the unique configuration of the metaphyseal element having wall segments that include substantially flat outer surfaces provides a configuration that allows removal of the prosthesis when required in a manner that disturbs a minimum of bone in the metaphysis.

In one embodiment, the metaphyseal element includes a generally "V" shaped cross-sectional configuration that may be defined as a trapezoidal solid (or frame), defined by four sides or aspects of the trapezoidal solid, a distal surface of the joint head and a proximal end of the shaft. In one embodiment the metaphyseal element is oriented with respect to the head and the stem of the device so as to present a configuration of a box having a substantially flat anterior side or aspect, a substantially flat posterior side or aspect, two open ends, a first defining in part a medial side or aspect that includes a medial aspect aperture and a second defining in part a lateral side or aspect that includes a lateral aspect aperture. Alternately the configuration of the metaphyseal element when viewed laterally or medially may be described as tubular, rectangularly tubular or as having an irregularly rectangular cross section.

In one embodiment the metaphyseal element defines a bone graft pocket defined by a pair of wall elements having a generally "V" shaped cross-sectional configuration defined in part as the region between the diverging walls. A relatively large lateral aspect aperture is formed on a lateral side or aspect of the metaphyseal element. The lateral aspect aperture is configured to permit introduction of and/or protrusion of bone graft material through the medial aspect of the metaphyseal element of the device. An aperture is also formed in a medial aspect of the metaphyseal element, the aperture configured to permit introduction of and/or protrusion of bone graft material through the medial aspect of the metaphyseal element of the device.

Upon installation of the prosthesis of the present invention, bone graft material is placed between the walls of the metaphyseal element of the device, filling the bone graft pocket in such a manner that the bone graft material is, due to the unique structure and arrangement of the metaphyseal element of the device, supported within the bone graft pocket and protruding from both the lateral aspect aperture and the medial aspect aperture formed generally at a convergence of the divergent walls forming a generally "V" shaped cross-sectional configuration, or alternately at the throat of the generally "U" shaped cross-sectional configuration. Upon impaction of the metaphyseal element of the device into the metaphysic of a bone, the bone graft material is compressed within the bone graft pocket and against the native bone into which the device is being impacted. To complement the interference fit, the bone graft material will typically be placed within the bone graft pocket such that it protrudes from the pocket both medially and laterally, thus allowing the bone graft to be compressed within the bone graft pocket both medially and laterally upon insertion.

The unique structure and arrangement of the walls of the metaphyseal element of the device and the resulting orientation of a bone graft pocket defined between the walls of the metaphyseal element which is formed generally on a medial-lateral plane that runs substantially parallel to the length of the bone, (the medial-lateral plane), permits protrusion of the bone graft material from the metaphyseal element of the device along a substantially medial-lateral plane. The unique structure and arrangement of the walls of the metaphyseal element of the device take advantage of the fact that the dimensions of the metaphyseal element of the device, like the bone they are designed to be implanted in, are greater across a medial-lateral plane than they are across an anterior-posterior plane. The unique structure and arrangement of the walls of the metaphyseal element of the device provides additional advantage over the prior art, which to the extent that it teaches an aperture through which bone graft material may be passed through or held with respect to the bone, does so on an anterior-posterior plane that runs substantially parallel to the length of the bone, (the anterior-posterior plane). The unique structure and arrangement of the walls of the metaphyseal element of the device provide improved increased prosthesis surface area for bony in-growth. The unique structure and arrangement of the walls also provide a configuration adaptable to supporting a protrusion of bone graft material from the metaphyseal element of the device for compaction along a substantially medial-lateral plane when the metaphyseal element is impacted into the surrounding native bone. Additionally, the unique structure and arrangement of the bone graft pocket formed between walls, the proximal surface of the stem and the distal surface of the head provide a structure into which bone graft material may be packed in such a manner that it is supported within bone graft pocket such that the bone graft material will not be displaced into the shaft of the bone upon insertion in the bone but rather will support the bone graft material so that it may protrude from the metaphyseal element of the device for compression against the native bone and within the bone graft pocket along a substantially medial-lateral plane.

Due in part to the configuration and orientation of the metaphyseal element of the prosthesis, a press-fit may be achieved between the metaphyseal element of the prosthesis and the corresponding metaphyseal element of the bone by packing bone graft material within the bone graft pocket of the prosthesis and about the metaphyseal element of the prosthesis until the desired fit is achieved. The subsequent osseous integration between native bone, bone graft material and metaphyseal element of the prosthesis keeps the prosthesis from loosening, settling or rotating. Bone graft material is readily available in most arthroplasty procedures. For example, in a reverse shoulder arthroplasty, the head of the humerus is separated from the remaining bone. Bone graft material can be harvested from the head and used in achieving the press-fit between the metaphyseal element of the prosthesis and the corresponding metaphyseal element of the bone as discussed herein.

In the one embodiment, the metaphyseal element also includes a plurality of minor apertures configured as slots or holes located anteriorly, posteriorly and/or medially, for providing vascular access for bone graft that has been placed within the bone graft pocket region of the prosthesis, to increase the surface area of the prosthesis onto which bone can integrate, to accommodate the insertion of bone graft around the prosthesis, and/or to serve as tying points for suture material.

The prosthesis of the present invention may also include a cap that may be secured to a lateral aspect metaphyseal element of the prosthesis over the lateral aspect aperture to provide structural support for reattachment of the greater tuberosity when needed (as in the case of fracture). The proximal humerus bone becomes increasingly hollow from the inside out with advancing patient age. As such, when an elderly patient sustains a proximal humerus fracture the greater tuberosity is often just a shell of thin cortical bone without much remaining cancellous bone. In these cases, the cap or plug, may be used to provide structural support, allowing the greater tuberosity to heal in a more anatomically correct position. The cap or plug may include slots or holes to allow intramedullary blood supply access to the healing fragment of the greater tuberosity, to support any bone graft material that may be added between the medial surface thereof and the lateral aspect of the cap, and to serve as suture tying points for reattachement of the tuberosities or soft tissue. The cap may also be solid; it could be used to fill the window in cases where there is not enough bone graft available—as in the elderly, osteopenic patient. The cap also includes a roughened surface to prevent the tuberosity fragment from migrating before it heals.

The present invention is also directed to a method for performing an arthroplasty, and more particularly to a method for implanting a prosthesis that includes a stem, a metaphyseal element attached at a proximal end of the stem, the metaphyseal element defining, at least in part, a bone graft pocket, the method including the steps of inserting the stem of the prosthesis into a shaft of a long bone, packing the bone graft pocket of the metaphyseal element with bone graft material, packing additional bone graft material around the metaphyseal element, and impacting the metaphyseal element of the prosthesis into the cavernous metaphyseal region of the bone achieving a press-fit between the metaphyseal element of the prosthesis and the cavernous metaphyseal region of the bone.

In another embodiment a method for press-fitting a shoulder prosthesis in a primary arthroplasty, the method includes the steps of removing the humeral head, harvesting bone graft material from the humeral head, applying harvested bone graft material within and/or around a metaphyseal element of the shoulder prosthesis and impacting the shoulder prosthesis with bone graft into the diaphysis.

DETAILED DESCRIPTION

Figure 1:
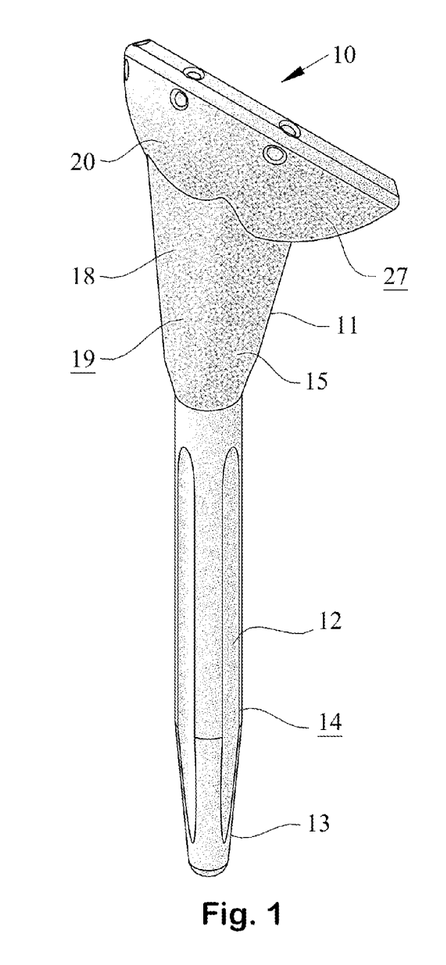
FIG. 1 is a representative perspective view of a reverse shoulder prosthesis according to the present invention.
Figure 2:
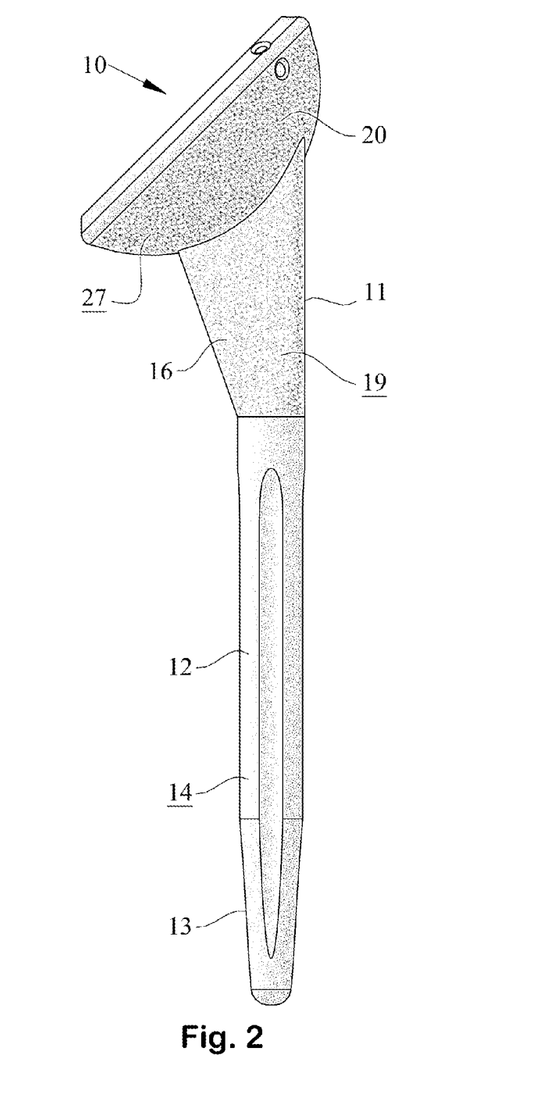
FIG. 2 is a representative side view of a reverse shoulder prosthesis according to the present invention.
Figures 3, 4:
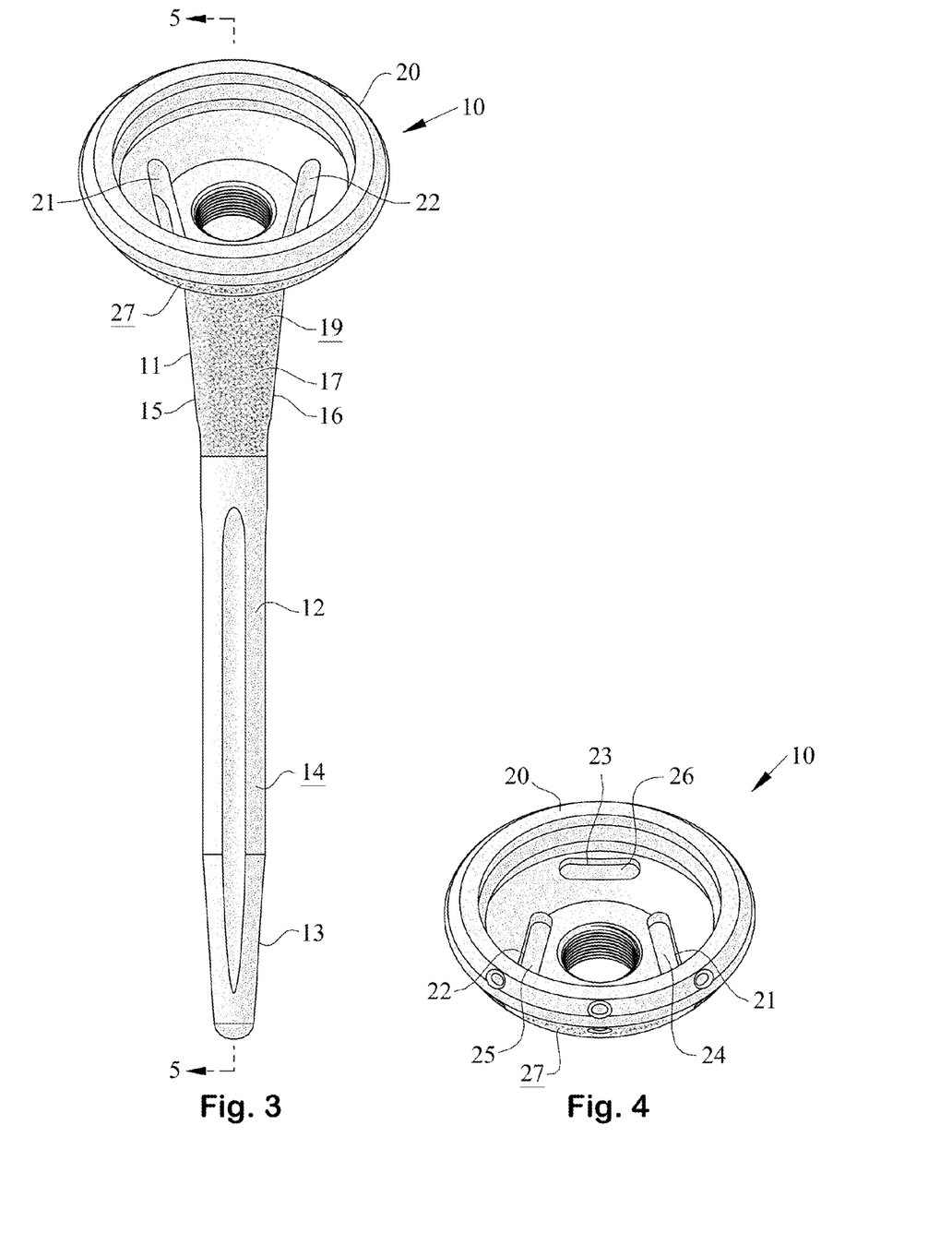
Fig. 3 is a representative medial view of a reverse shoulder prosthesis according to the present invention.
Fig. 4 is a representative top view of a reverse shoulder prosthesis according to the present invention.

Referring to FIGS. 1-3, prosthesis 10 is shown including metaphyseal element 11 attached at a proximal end of stem 12. Stem 12 includes distal end 13 to aid in the insertion of the device in the medullary cavity of a long bone. In a preferred embodiment, stem 12 includes polished surface 14 again to aid in the insertion of the device as well as removal of prosthesis 10 when indicated. Metaphyseal element 11 includes an anterior aspect that is defined by first wall element 15 and as seen in FIG. 1, and a posterior aspect defined by second wall element 16 and as seen in FIG. 2. Referring to FIG. 1, metaphyseal element 11 is shown also including a lateral aspect defined by third wall element 18 which as seen attaches to first wall element 15. Similarly as seen in FIG. 3, metaphyseal element 11 is shown also including a medial aspect defined by fourth wall element 17. As seen in FIG. 1, first wall element 15 and third wall element 18 are each defined in part by a substantially flat outer face each face exhibiting a textured metaphyseal element surface 19. Similarly second wall element 16, seen in FIG. 2, and fourth wall element 17, seen in FIG. 3 are each defined in part by a substantially flat outer face each face exhibiting a textured metaphyseal element surface 19.

Referring again to FIGS. 1-3, prosthesis 10 is shown including joint base member 20 attached at a proximal end of metaphyseal element 11. Joint base 20 includes textured surface 27. Textured surface 19 of metaphyseal element 11 and textured distal surface 27 of joint base 20 may be formed by a mechanical, chemical or coating process to promote bony in-growth against the respective surface.

Referring to FIG. 4, in the preferred embodiment, osteotome slots 21, 22, and 23 include a frangible partition, first frangible partition 24, second frangible partition 25 and third frangible partition 26 respectively. In other alternate embodiments of the invention, the prosthesis may include only the osteotome slots without the frangible partitions. The frangible partition may be formed as a thin metal layer or a frangible wall composed of cement, for instance a polymethylmethacrolate cement, or plastic which would serve as a barrier with the purpose of keeping foreign material, particularly polyethylene debris, from finding its way through the osteotome slot into the bone over time. The surface of the partition that is oriented towards the bone would preferably include a roughened surface consistent with the surrounding surfaces of joint base member 20 to promote bony in-growth against the surface. Alternately a "blind" hole may be created by simply filling a portion of the osteotome slot with a cement or plastic thereby forming a penetrable wall against which bony growth may readily occur.

Referring to FIG. 4, prosthesis 10 is shown including joint base member 20 including first osteotome slot 21, second osteotome slot 22 and third osteotome slot 23. As seen in FIG. 3, first osteotome slot 21 and second osteotome slot 22 are located proximate to and, as seen in FIG. 3, run substantially parallel to first wall element 15 and second wall element 16 respectively. Similarly, third osteotome slot 23 with third frangible partition 26 is located proximate to and, as seen in FIGS. 5 and 6, runs substantially parallel to fourth wall element 17.

Figure 5:
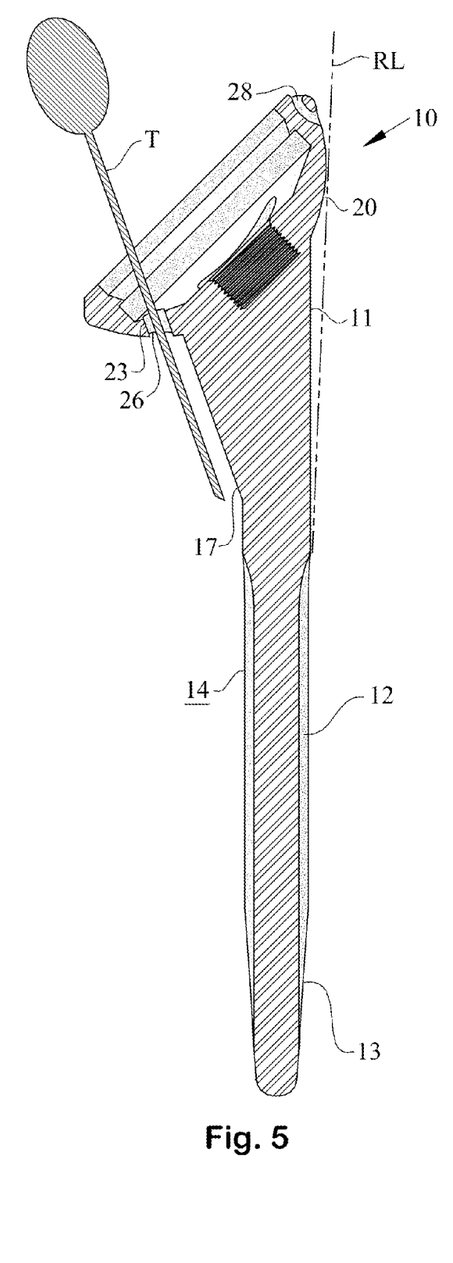
FIG. 5 is a representative side cutaway view of a reverse shoulder prosthesis according to the present invention.

Referring to FIG. 5, prosthesis 10 is shown in cross section. Prosthesis 10 includes metaphyseal element 11 attached at a proximal end of stem 12. Stem 12 is shown having distal end 13 and polished surface 14. Joint base member 20 is shown formed contiguous to and extending from a proximal end of metaphyseal element 11. As seen in FIG. 5, in the event that removal of prosthesis 10 is required, an osteotome or other tool T may be used to penetrate each of the frangible partitions extending the tool T along side the adjacent wall segment breaking metaphyseal element 11 free of the surrounding bone, (not shown). FIG. 5 shows tool T inserted into and through third osteotome slot 23 having penetrated third frangible partition 26 to extend alongside fourth wall element 17 in just such a manner. It will be appreciated that an aperture is not required along the lateral face of metaphyseal element 11 as a tool may be readily inserted along removal line RL and worked against the lateral aspect of metaphyseal element 11 defined by third wall element 18 to free the lateral aspect of metaphyseal element 11 from any bony in-growth.

Figure 6:
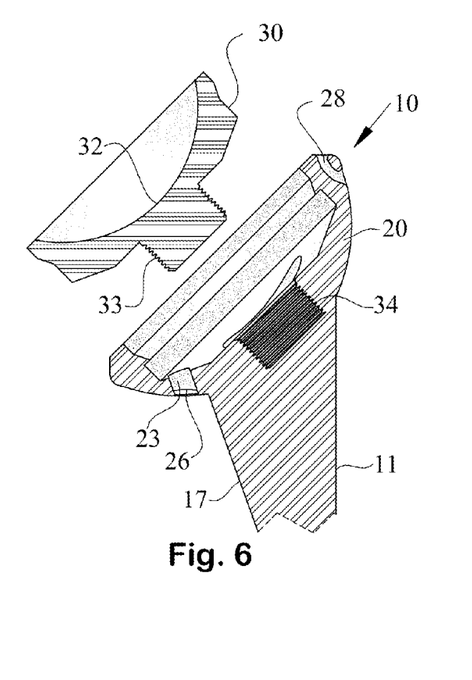
FIG. 6 is a representative side cutaway detail view of a reverse shoulder prosthesis according to the present invention.

Referring to FIG. 6, a detailed cross-section of a proximal end of prosthesis 10 is shown. Joint base member 20 is shown formed contiguous to and extending from a proximal end of metaphyseal element 11. Joint articulation member 30 is formed as a polymeric socket which includes threaded post 33 which is adapted to threadedly engage with threaded socket 34. As shown, joint articulation member 30 also includes concave surface 32 which is configured to articulate against a corresponding hemispherical implant, (not shown). FIG. 6 also shows suture apertures 28 configured to permit passage of a suture, (not shown) that may be used in reattachment of bony structure.

Figure 7:
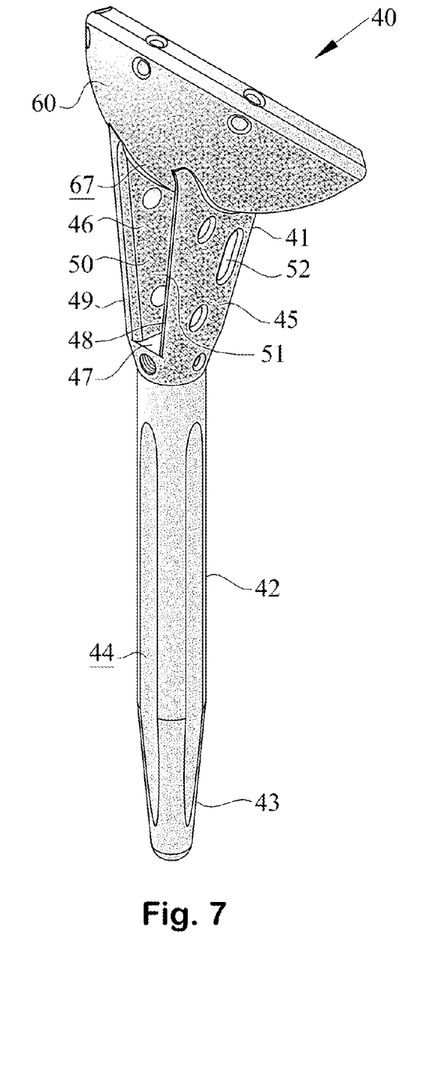
FIG. 7 is a representative perspective view of a reverse shoulder prosthesis according to the present invention.
Figure 8:
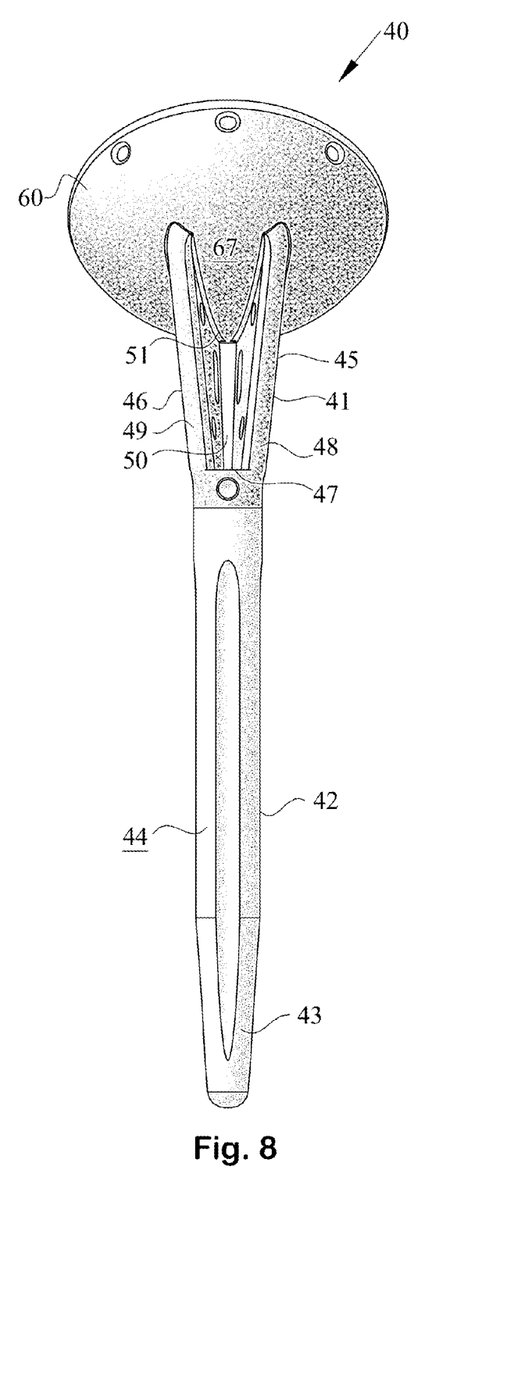
FIG. 8 is a representative lateral view of a reverse shoulder prosthesis according to the present invention.
Figure 9:
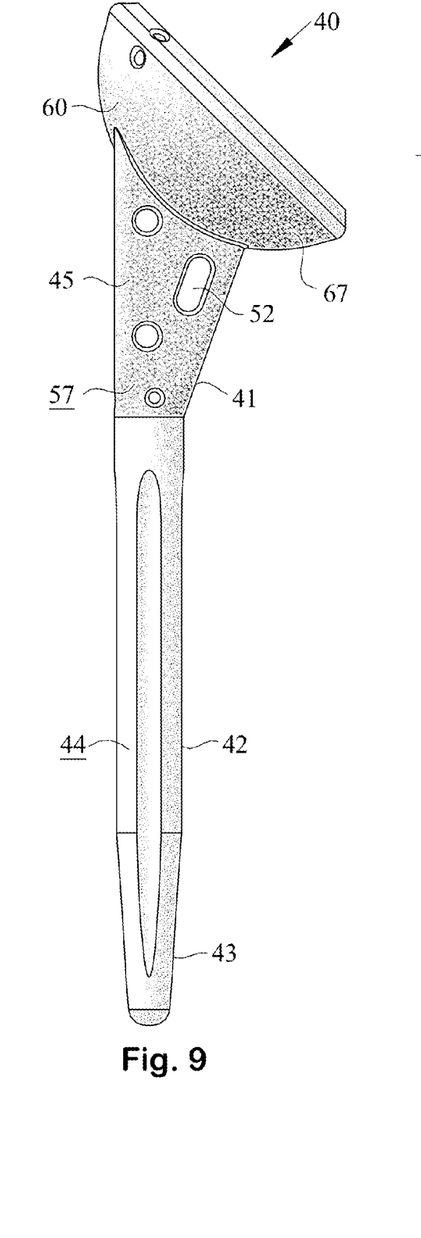
FIG. 9 is a representative side view of a reverse shoulder prosthesis according to the present invention.

Referring to FIGS. 7-9, prosthesis 40 is shown including metaphyseal element 41 attached at a proximal end of stem 42. Stem 42 includes distal end 43 to aid in the insertion of the device in the medullary cavity of a long bone. In a preferred embodiment, stem 42 includes polished surface 44 which aids in the prevention of bony adherence occurring against stem 42, which would make prosthesis 40 more difficult to remove. Metaphyseal element 41 includes a pair of diverging wall elements, first wall element 45 defining an anterior aspect and second wall element 46 defining a posterior aspect, (seen in FIGS. 7 and 8). As seen in FIGS. 7-9 first wall element 45 and second wall element 46 are each defined in part by a substantially flat outer face, each face exhibiting a textured metaphyseal element surface 57 shown in FIG. 9.

Referring to FIGS. 7 and 8, bone graft pocket 50 is defined by a space between first wall element 45, second wall element 46, distal surface 67 of joint base member 60 and a proximal end 47 of stem 42. Lateral aspect aperture 51 is defined by first wall lateral edge 48 of first wall element 45 and second wall lateral edge 49 of second wall element 46. In the embodiment shown in FIGS. 7-10, bone graft material, (not shown), may be packed into bone graft pocket 50 through lateral aspect aperture 51 prior to impacting prosthesis 40 into the long bone, (not shown). FIGS. 7 and 9 show vascularization apertures 52 formed through first wall element 45 and second wall element 46 so that the apertures extend from medial to lateral.

Figure 10:
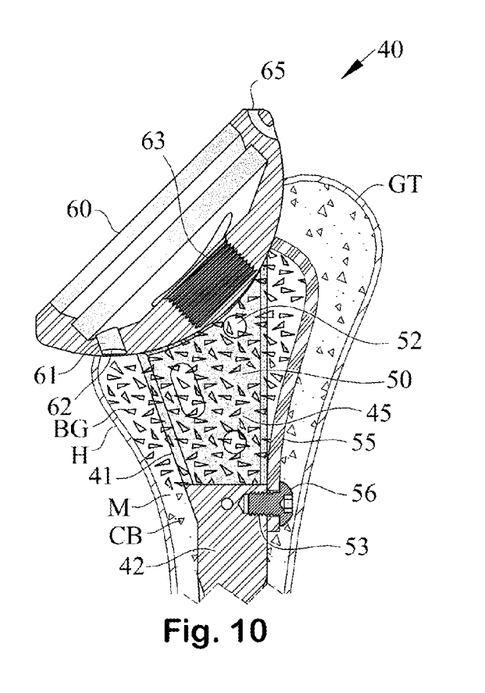
FIG. 10 is a representative side cutaway detail view of a reverse shoulder prosthesis according to the present invention.

Referring to FIG. 10, a detailed cross-section of a proximal end of prosthesis 40 including joint base member 60 formed at a proximal end of metaphyseal element 41. Shaft 42 and metaphyseal element 41 are shown impacted into a proximal end of humerus bone H. According to one methodology of the present invention, bone graft pocket 50 is packed with bone graft material BG to achieve a press fit when prosthesis 40 is impacted into the proximal end of humerus bone H. In those instances where the greater tuberosity GT has detached, cap 55 may be attached by threaded fastener 56 that cooperates with threaded aperture 53 to attach cap 55 to a lateral aspect of metaphyseal element 41 to provide increased support for reattachment of the greater tuberosity GT against metaphyseal element 41. Cap 55 may be configured as a solid closure element or in the alternative may include one or more apertures through which bone graft material may extend and through which re-vascularization of the bone graft material may occur. Suture aperture 65 is adapted to provide an anchor for sutures, (not shown), that may be employed for reattachment of greater tuberosity GT and/or connective tissue that may surround the joint. Vascularization apertures 52 are shown formed through first wall element 45.

Also shown in FIG. 10 is osteotome slot 61 including frangible partition 62. FIG. 10 also shows joint base member 60 including threaded socket 63 configured for threaded engagement with a threaded post of a joint articulation member including a socket element as typified by the joint articulation member shown and previously described in the discussion of FIG. 6.

Figure 11:
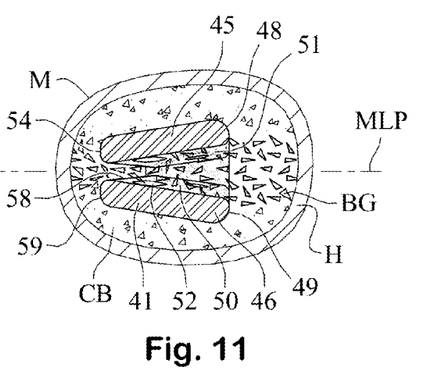
FIG. 11 is a representative top cutaway detail view of a reverse shoulder prosthesis according to the present invention.

FIG. 11 is a representative top cross-sectional view of first wall element 45 and second wall element 46 forming a generally "V" shaped cross-sectional configuration of metaphyseal element 41. First wall element 45 includes lateral edge 48 and medial edge 54. Similarly second wall element 46 includes lateral edge 49 and medial edge 59. Bone graft material BG is introduced into bone graft pocket 50 through lateral aspect aperture 51 in such a manner that bone graft material BG protrudes through lateral aspect aperture 51, defined in part by lateral edges 48 and 49, and medial aspect aperture 58, defined in part by medial edges 54 and 59, generally along medial-lateral plane MLP. Bone graft material BG is supported within bone graft pocket 50 from displacing distally into the shaft of the bone or proximally of metaphysis M.

Upon impaction of metaphyseal element 41, protruding bone graft is compressed against compact bone CB and within bone graft pocket 50 to achieve a press-fit of metaphyseal element 41 within metaphysis M of the humerus H. As bone repair matures bone graft material BG undergoes vascularization through lateral aspect aperture 51, medial aspect aperture 58 and vascularization apertures 52. Vascularization apertures 52 may also be used as needed for tying points for sutures.

Figures 12, 13:
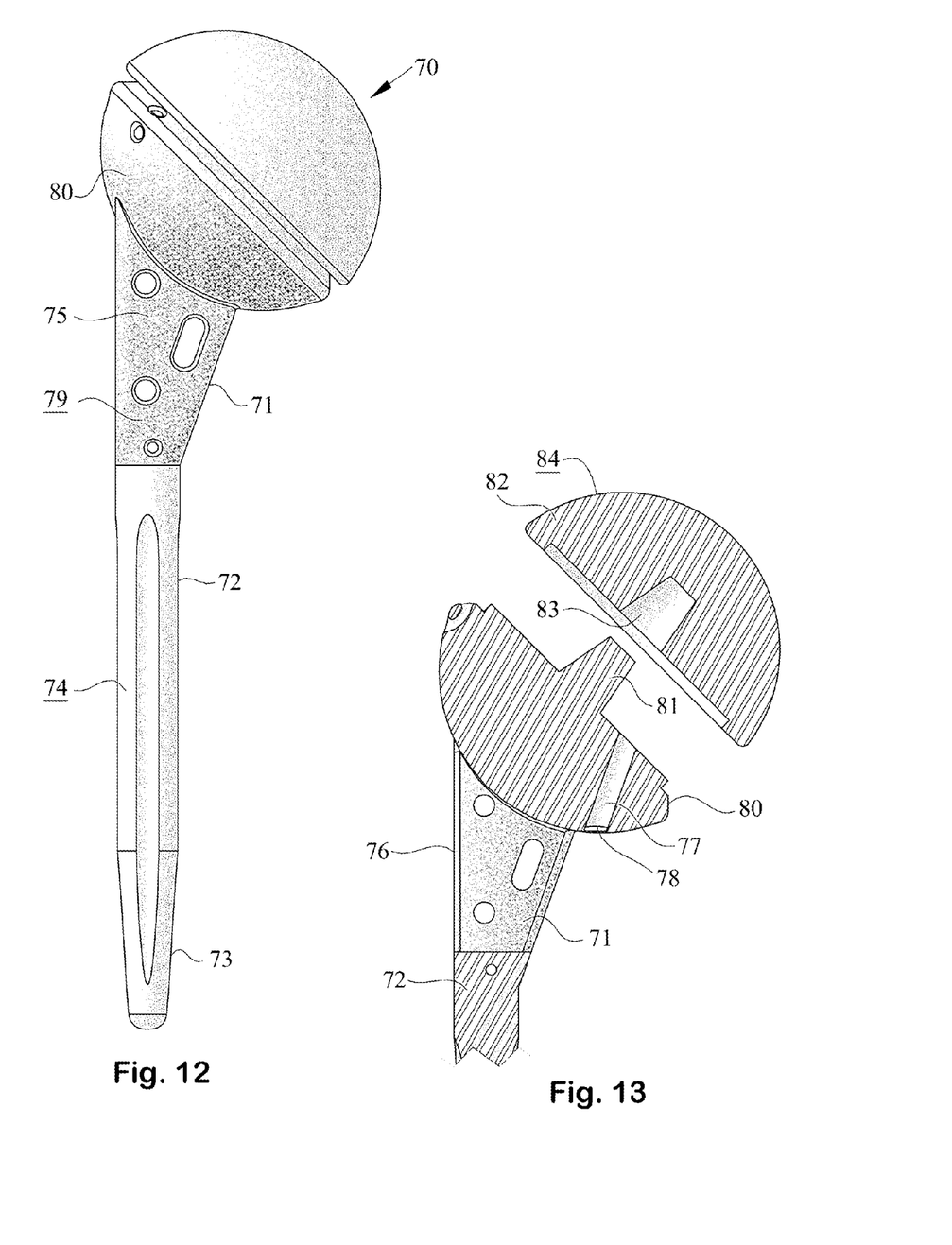
FIG. 12 is a representative side view of a reverse shoulder prosthesis according to the present invention.
FIG. 13 is a representative side cutaway detail view of a reverse shoulder prosthesis according to the present invention.

FIGS. 12 and 13 show an alternate embodiment of the invention configured as a standard or primary shoulder prosthesis. Prosthesis 70 includes metaphyseal element 71 extending proximally from stem 72. Stem 72 includes distal end 73 and polished surface 74, (shown in FIG. 12). Metaphyseal element 71 includes first wall element 75, (shown in FIG. 12), defining in part an anterior aspect of metaphyseal element 71 and second wall element 76, (shown in FIG. 12), defining in part a posterior aspect of metaphyseal element 71. Joint base member 80 is connected to metaphyseal element 71 and as seen in FIG. 13 includes primary surface 85. Tapered post 81 is formed on and extends from primary surface 85 and is adapted to engage tapered socket 83 formed in a distal surface of cap member 82. Cap member 82 includes concave torispherical articulation surface 84 configured for articulation against the glenoid.

Figure 14:
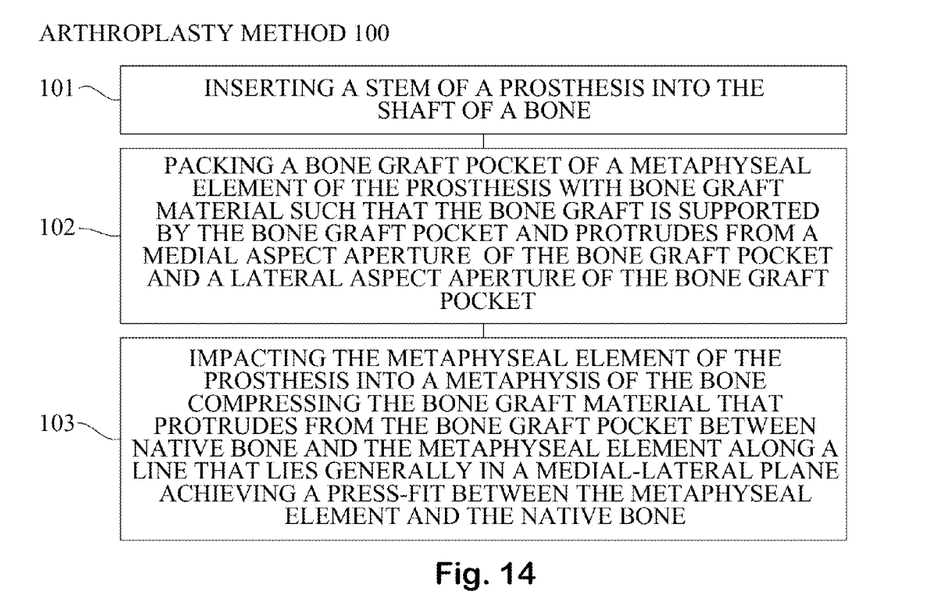
FIG. 14 is a schematic flow diagram depicting steps of an arthroplasty method for implanting a prosthesis according to the present invention.

FIG. 14 shows ARTHROPLASTY METHOD 100 including the steps of INSERTING A STEM OF A PROSTHESIS INTO THE SHAFT OF A BONE 101, PACKING A BONE GRAFT POCKET OF A METAPHYSEAL ELEMENT OF THE PROSTHESIS WITH BONE GRAFT MATERIAL SUCH THAT THE BONE GRAFT IS SUPPORTED BY THE BONE GRAFT POCKET AND PROTRUDES FROM A MEDIAL ASPECT APERTURE OF THE BONE GRAFT POCKET AND A LATERAL ASPECT APERTURE OF THE BONE GRAFT POCKET 102, and IMPACTING THE METAPHYSEAL ELEMENT OF THE PROSTHESIS INTO A METAPHYSIS OF THE BONE COMPRESSING THE BONE GRAFT MATERIAL THAT PROTRUDES FROM THE BONE GRAFT POCKET BETWEEN NATIVE BONE AND THE METAPHYSEAL ELEMENT ALONG A LINE THAT LIES GENERALLY IN A MEDIAL-LATERAL PLANE ACHIEVING A PRESS-FIT BETWEEN THE METAPHYSEAL ELEMENT AND THE NATIVE BONE 103.

Figure 15:
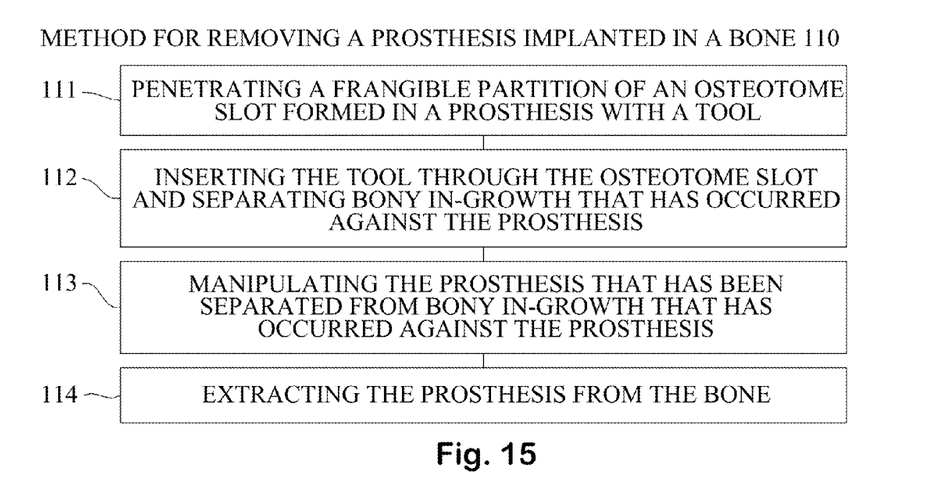
FIG. 15 is a schematic flow diagram depicting steps of an arthroplasty method for implanting a prosthesis according to the present invention.

FIG. 15 shows a METHOD FOR REMOVING A PROSTHESIS IMPLANTED IN A BONE 110 including the steps of PENETRATING A FRANGIBLE PARTITION OF AN OSTEOTOME SLOT FORMED IN A PROSTHESIS WITH A TOOL 111, INSERTING THE TOOL THROUGH THE OSTEOTOME SLOT AND SEPARATING BONY IN-GROWTH THAT HAS OCCURRED AGAINST THE PROSTHESIS 112, MANIPULATING THE PROSTHESIS THAT HAS BEEN SEPARATED FROM BONY IN-GROWTH THAT HAS OCCURRED AGAINST THE PROSTHESIS 113, and TRACTING THE PROSTHESIS FROM THE BONE 114.

The foregoing description of the illustrated embodiments has been presented for purposes of illustration and description. It is not intended to be exhaustive or to limit the invention to the precise form or to exemplary embodiment(s) and implementation(s) disclosed. Numerous modifications and variations will be apparent to practitioners skilled in this art. Process steps described might be interchangeable with other steps in order to achieve the same result. At least one preferred embodiment was chosen and described in order to best explain the principles of the invention and a best mode of practical application, thereby to enable others skilled in the art to understand the invention for various embodiments and with various modifications as are suited to the particular use or implementation contemplated. It is intended that the scope of the invention be defined by the claims appended hereto and their equivalents. Reference to an element in the singular is not intended to mean "one and only one" unless explicitly so stated, but rather means "one or more." Moreover, no element, component, or method step in the present disclosure is intended to be dedicated to the public regardless of whether the element, component, or method step is explicitly recited in the following claims. No claim element herein is to be construed under the provisions of 35 U.S.C. Sec. 112, sixth paragraph unless the element is expressly recited using the phrase "means for . . . ."

What is claimed is:

1. A prosthesis comprising:
a stem;
a metaphyseal element attached at a proximal end of the stem, the metaphyseal element including a first wall element connected to and extending proximally from the stem and a second wall element connected to and extending proximally from the stem;
a joint base member attached at a proximal end of the metaphyseal element;
a joint articulation member attached to the joint base member;
a first osteotome slot formed through the joint base member proximate to and substantially parallel to an exterior surface of the first wall element, the first osteotome slot including a frangible partition; and
a second osteotome slot formed through the joint base member proximate to and substantially parallel to an exterior surface of the second wall element, the second osteotome slot including a frangible partition.

2. The prosthesis of claim 1 further comprising:
a medial aspect aperture defining in part a medial aspect of the metaphyseal element;
a lateral aspect aperture defining in part a lateral aspect of the metaphyseal element; and
a bone graft pocket formed in the metaphyseal element along a substantially medial-lateral plane, the bone graft pocket formed proximal to the stem, distal to the joint base member, the bone graft pocket defined between the first wall element, the second wall element, the lateral aspect aperture and the medial aspect aperture.

3. The prosthesis of claim 1 further comprising a bone graft pocket defined between the first wall element and the second wall element.

4. The prosthesis of claim 1 further comprising:
the joint base member further comprising a post; and
the joint articulation member further comprising a cap member including a socket configured for a cooperating fit with the post of the joint base member, the cap further comprising a concave articulation surface.

5. The prosthesis of claim 1 wherein the first wall element and the second wall element further comprise a plurality of vascularization apertures.

6. A prosthesis comprising:
a stem;
a metaphyseal element attached at a proximal end of the stem, the metaphyseal element including a first diverging wall element including a substantially flat outer face, the metaphyseal element further comprising a second diverging wall element including a substantially flat outer face;
a medial aspect aperture defining in part a medial aspect of the metaphyseal element;
a lateral aspect aperture defining in part a lateral aspect of the metaphyseal element;
a joint base member attached at a proximal end of the metaphyseal element;
a bone graft pocket formed in the metaphyseal element along a substantially medial-lateral plane, the bone graft pocket formed proximal to the stem, distal to the joint base member, the bone graft pocket defined between the first diverging wall element, the second diverging wall element, the medial aspect aperture and the lateral aspect aperture; and
a joint element attachable to the joint base member.

7. The prosthesis of claim 6 further comprising
a first osteotome slot formed in the joint element proximate to and substantially parallel to the substantially flat face of the first wall element;
a second osteotome slot formed in the joint element proximate to and substantially parallel to the substantially flat face of the second wall element; and
a third osteotome slot formed in the joint base member proximate to and substantially parallel to the medial aspect of the metaphyseal element.

8. The prosthesis of claim 6 further comprising:
a first osteotome slot formed through the joint element proximate to and substantially parallel to the substantially flat face of the first wall element, the first osteotome slot including a frangible partition, the frangible partition of the first osteotome slot forming a portion of a distal surface of the joint base member;
a second osteotome slot formed through the joint element proximate to and substantially parallel to the substantially flat face of the second wall element, the second osteotome slot including a frangible partition, the frangible partition of the second osteotome slot forming a portion of the distal surface of the joint base member; and
a third osteotome slot formed in the joint base member proximate to and substantially parallel to a medial edge of the first diverging wall element and a medial edge of the second diverging wall element, the third osteotome slot including a frangible partition, the frangible partition of the third osteotome slot forming a portion of the distal surface of the joint base member.

9. A prosthesis adapted to permit introduction of bone graft material into and protrusion of bone graft material from a metaphyseal element of the prosthesis, the prosthesis comprising:
a stem;
a metaphyseal element attached at a proximal end of the stem, the metaphyseal element further comprising a first wall element, the first wall element including a substantially flat outer face, the metaphyseal element further comprising a second wall element, the second wall element including a substantially flat outer face, the first wall element diverging from the second wall element as the first wall element and the second wall element extend proximally from the stem;
a medial aspect aperture defining in part a medial aspect of the metaphyseal element;
a lateral aspect aperture defining in part a lateral aspect of the metaphyseal element;
a joint base member attached at a proximal end of the metaphyseal element;
a bone graft pocket formed in the metaphyseal element along a substantially medial-lateral plane, the bone graft pocket formed proximal to the stem, distal to the joint base member, the bone graft pocket being further defined by the first wall element, the second wall element, the medial aspect aperture and the lateral aspect aperture;
a first osteotome slot formed in the joint base member proximate to and substantially parallel to the outer face of the first wall element;
a second osteotome slot formed in the joint base member proximate to and substantially parallel to the outer face of the second wall element; and
a joint element attachable to the joint base member.

10. The prosthesis of claim 9 further comprising:
the first osteotome slot including a frangible partition, the frangible partition of the first osteotome slot forming a portion of a distal surface of the joint base member;
the second osteotome slot including a frangible partition, the frangible partition of the second osteotome slot forming a portion of the distal surface of the joint base member; and
a third osteotome slot formed in the joint base member proximate to and substantially parallel to a medial edge of the first diverging wall element and a medial edge of the second diverging wall element, the third osteotome slot including a frangible partition, the frangible partition of the third osteotome slot forming a portion of the distal surface of the joint base member.

* * * * *